US006699200B2

(12) United States Patent
Cao et al.

(10) Patent No.: US 6,699,200 B2
(45) Date of Patent: Mar. 2, 2004

(54) IMPLANTABLE MEDICAL DEVICE WITH MULTI-VECTOR SENSING ELECTRODES

(75) Inventors: Jian Cao, Maplewood, MN (US); Brian B. Lee, Golden Valley, MN (US); Spencer R. Hurd, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 405 days.

(21) Appl. No.: 09/797,031

(22) Filed: Mar. 1, 2001

(65) Prior Publication Data

US 2001/0034487 A1 Oct. 25, 2001

Related U.S. Application Data

(60) Provisional application No. 60/186,235, filed on Mar. 1, 2000.

(51) Int. Cl.[7] ............................. A61B 5/02; A61B 19/00
(52) U.S. Cl. ........................................ 600/508; 128/899
(58) Field of Search ........................ 600/508, 506, 600/510, 511, 512, 513, 514, 515, 516, 517, 518, 519, 520, 521, 522, 523, 524, 525, 526, 527, 528; 128/897, 898, 899

(56) References Cited

U.S. PATENT DOCUMENTS

| | | |
|---|---|---|
| 4,223,678 A | 9/1980 | Langer et al. |
| 4,407,288 A | 10/1983 | Langer et al. |
| 4,556,063 A | 12/1985 | Thompson et al. |
| 5,226,425 A | 7/1993 | Righter |
| 5,289,824 A | 3/1994 | Mills et al. |
| 5,313,953 A | 5/1994 | Yomtov et al. |
| 5,331,966 A | 7/1994 | Bennett et al. |
| 5,333,616 A | 8/1994 | Mills et al. |
| 5,365,935 A | 11/1994 | Righter et al. |
| 5,404,877 A | 4/1995 | Nolan et al. |
| 5,411,031 A | 5/1995 | Yomtov |
| 5,417,717 A | 5/1995 | Salo et al. |
| 5,464,431 A | 11/1995 | Adams et al. |
| 5,464,434 A | 11/1995 | Alt |
| 5,511,553 A | 4/1996 | Segalowitz |
| 5,513,645 A | 5/1996 | Jacobson et al. |
| 5,518,001 A | 5/1996 | Snell |
| 5,810,014 A * | 9/1998 | Davis et al. ................. 600/508 |
| 5,921,937 A * | 7/1999 | Davis et al. ................. 600/508 |
| 5,987,352 A | 11/1999 | Klein et al. |
| 6,501,983 B1 * | 12/2002 | Natarajan et al. ........... 600/517 |

OTHER PUBLICATIONS

Leitch, James, *PACE*, "Feasibility of an Implantable Arrhythmia Monitor," vol. 15, Dec. 1992 (15:588), pp. 2232–35.
Poster presentation of North American Society of Pacing and Electrophysiology (NASPE), "Subcutaneous, Bipolar 'Pseudo–ECG' Recordings using an Implantable Monitoring System," Apr. 1992, Part II, p. 588.

* cited by examiner

*Primary Examiner*—Thomas Denion
*Assistant Examiner*—Daniel Robinson
(74) *Attorney, Agent, or Firm*—Elisabeth L. Belden; Girma Wolde-Michael

(57) ABSTRACT

A medical device for multi-vector sensing of cardiac depolarization signals is disclosed. Specialized algorithm is implemented to enhance multi-vector electrode sensing. Further a geometric shape is optimized to enable space-volume efficiencies for deployment and navigation of the medical device for implant in a patient.

9 Claims, 5 Drawing Sheets

IMPLANTABLE MEDICAL DEVICE WITH MULTI-VECTOR SENSING ELECTRODES

This application claims the benefit of Provisional application No. 60/186,235 filed Mar. 1, 2000.

FIELD OF THE INVENTION

The present invention relates to implantable medical devices. Specifically, the invention relates to an Insertable Loop Recorder (ILR) for sensing physiologic signals with minimal intrusion into a patient's body. More specifically, the invention relates to a geometrically optimized space-volume efficient device adapted for ease of deployment in small incisions in the patient's body. The geometry and structure of the ILR is also adapted for optimal distribution of electrodes configured an enhanced for multi-vector sensing.

BACKGROUND OF THE INVENTION

Syncopal episodes and cardiac arrhythmias are particularly problematic for diagnostic physicians to observe in real time in their patients. These events can be of short duration and sudden onset, and may occur very infrequently. Holter monitors are well known in the art for continuously monitoring electrocardiograms over a 24 or 48-hour period of time. These monitors, however, are bulky and when, applied externally to the body, interfere with the patient's normal life, making them impractical for long-term use. Further, patient compliance cannot always be guaranteed, and is a common problem in their use. Problems with these and other external monitors and associated recorders also include the inability of some patients to tolerate the attendant skin irritation. Removal of these devices may be needed for example, for showering or to conduct other daily activities. All these problems come into focus any time a patient needs long-term monitoring to detect a non-physiologic episode (whether intermittent, infrequent, or both), all these problems come into focus.

Many attempts have been made to address some of these problems only with limited success. One approach is disclosed in the Mills, et al patents (U.S. Pat. Nos. 5,333,616; 5,289,824 and 5,111,396) for a wrist-worn monitor for ECG's which include features for patient triggering and microprocessor determination of event types (QRS detection). Wrist-worn devices are also shown in U.S. Pat. Nos. 5,226,425 and 5,365,935, issued to Righter. Further, Jacobsen, et al in U.S. Pat. No. 5,513,645 describes multiple resolution storage for ECG's and Snell's U.S. Pat. No. 5,518,001 generally describes a patient-triggered recording device with multiple sensors. The Yomatov patents, U.S. Pat. Nos. 5,411,031 and 5,313,953, appear to focus on beat-to-beat timing records and suggest the use of an arrhythmia detector, as well as the possibility of leadless electrodes for monitoring cardiac signals. Examples of an external monitor/recorder can be found in Segalowitz' patents, including U.S. Pat. No. 5,511,553, and Salo's U.S. Pat. No. 5,417,717. Another well-known event recorder is the "King of Hearts™" that records both pre- and post-episode data.

Monitoring of physiologic data can be conducted using implantable pulse generators or devices with leads in the heart for capturing cardiac data, including ECG. However, the expense and risk of implanting an intracardiac lead and/or a pacemaker with special monitoring functions is something both patients and physicians would prefer to avoid. Such devices, in addition to performing therapeutic operations, may monitor and transmit cardiac electrical signals (e.g., intracardiac electrograms, or EGMs) from the leads fixed in the patient's heart. It is generally common for implanted cardiac stimulation devices to send the EGM signals to a monitoring device, such as an external programmer, to allow a physician or other medical expert to analyze the heart's activity.

For example, U.S. Pat. No. 4,223,678, entitled *Arrhythmia Recorder for Use with an Implantable Defibrillator*, issued to Langer et al., discloses an arrhythmia record/playback component within an implantable defibrillator. ECG data is converted from analog to digital (A/D) form and stored in a first-in, first-out memory. When the defibrillator detects an arrhythmia episode, it disables the memory so that no further ECG data is recorded in the memory until a command is received from an external monitoring device. This command requests the implantable defibrillator to transmit the stored ECG data to the monitoring device via telemetry. Langer et al. in U.S. Pat. No. 4,407,288, discloses a programmable, microprocessor-based implantable defibrillator that senses and loads ECG data into a memory via a direct memory access operation. A processor analyzes this ECG data in the memory to detect the occurrence of an arrhythmia episode. Upon detection, the defibrillator may generate a therapy to terminate the arrhythmia episode and store the ECG data sequence of the episode for transmission to an external monitoring device and later study. In normal circumstances, when no arrhythmia episode is occurring, the defibrillator continuously overwrites the ECG data in the memory.

U.S. Pat. No. 4,556,063, to D. L. Thompson et al, teaches a pulse interval telemetry system capable of transmitting analog data, such as sensed EGM signals, without converting analog data to a digital numeric value. The Thompson et al. telemetry system is capable of sequentially transmitting both digital and analog data, individually and serially, in either an analog or a digital format, to a remote receiver. The features and capabilities of these pacemaker/defibrillator devices are well known, but the problems in long-term monitoring and recording of such episodes remain.

In the December 1992 Vol. 15 edition of PACE (15:588), a feasibility study was reported on implantable arrhythmia monitors and described in an article by Leitch et al. Then, at a chaired poster presentation of the North American Society of Pacing and Electrophysiology (NASPE), titled *Subcutaneous, Bipolar "Pseudo-ECG" Recordings using an Implantable Monitoring System*, an implantable monitoring system was described using a pacemaker that had been altered to use a point on the pacemaker casing as one electrode with a second electrode mounted on the connector block.

Further, a leadless implantable sensor for cardiac emergency warning is described in U.S. Pat No. 5,404,877 issued to Nolan et al. that detects heart events through impedance measurement that are sensed via a coil. See also Yomato et al, U.S. Pat. No. 5,313,953 that discloses a large but leadless implant.

With sufficient hardware and connections to the body, numerous other physiologic parameters may be sensed as is pointed out in U.S. Pat. No. 5,464,434 issued to Alt and U.S. Pat. No. 5,464,431 issued to Adams et al.

The Klein patent ('352), however, discloses the need for minimally intrusive long-term monitoring of a patient's non-physiologic episodes and their status. The '352 patent primarily relates to patients with cardiac arrhythmias and vasovagal syncope to provide sufficient evidence for diagnostic purposes and for research into the causes and effects of such episodes. Patients have come to accept long-term implants of these devices for the past number of years.

Using the ILRs, a cardiologist can use the ECG data as a guide for further therapy to match a patient's changing conditions to monitor either improvements or alterations of medical conditions. Such information can also be especially useful to the cardiologist in adjusting antiarrhythmic drug therapy to maximize the therapy and minimize side effects. Hence, the implantable cardiac patient monitor (ILR) of the '352 invention has proved capable of providing the cardiologist with heart rhythm information not previously available in the prior art.

An ILR, as currently configured, may be defined as an implantable, single use, programmable device for continuous recording of a patient's subcutaneous ECG during symptomatic and asymptomatic episodes. Most ILRs are small implantable devices that use material commonly used in the fabrication of other implantable devices, such as titanium. Typically, the dimensions will approximate 19 mm (h), 61 mm (L), and 8 mm (w).

During the implant the physician must consider a pocket site that will provide the patient comfort and preference while, at the same time, optimal signal amplitude. The incision must be able to accommodate the width of the device and the pocket must accommodate the length and thickness. To capture the ECG, the ILR has typically two flush-mounted sensing electrodes spaced at 38–39 mms apart. External leads are not used. The elongated, rectangular shape and the mounting of the electrodes are designed to provide ease of implantation, while the maximum separation of the electrodes is intended to provide high quality ECGs.

Achieving maximum diagnostic utility requires that the device's electrodes must be able to detect intracardiac waveforms of the greatest amplitude. Thus, the R and T-waves must be easily discernible with, at the same time, minimal detection of ambient noise whether from nearby electrical sources or myopotentials. Achieving these goals currently requires not only an optimal orientation of the ILR at and within an implant site, but also a manual setup with the use of the programmer. Secondly, even when an optimal orientation is achieved, it may not always be possible to maintain this orientation, due to patient motion, the effects of gravity, device migration, etc. Any one of these may compromise the quality of the ECG recording. Finally, there is a built-in limitation to the two-electrode system currently employed. Only one vector is available to detect and record an ECG tracing when only two electrodes are used. This fact limits where a pocket site may be located as well as the flexibility for recording ECG tracing from other vectors that might provide a better "view" for diagnostic purposes.

SUMMARY OF THE INVENTION

The present invention is an improvement, in relevant parts, on the algorithm disclosed in U.S. Pat. No. 5,331,966, issued to Bennett, et al in 1994 and incorporated herein in its entirety. Further, the present invention includes space-volume optimizing dimensions and structures to enable ease of implant optimal R-Wave sensing and signal recording.

The present invention relates to multi vector sensing of cardiac depolarization signals that form the basis of an ECG tracing, as opposed to the single vector sensing disclosed in the '352 patent. The preferably orthogonal distribution of electrode configuration disclosed in the present invention, with an improved algorithm, provides a more flexible and optimal system for sensing cardiac depolarizations. In addition, the present invention includes novel casing shapes that are structured to promote stability of the ILR within an incision or pocket post implant. The increased number of electrodes, preferably three without limitations, makes the ILR less susceptible to electrical interference and motion artifacts as well as less sensitive to the need for specific and exclusive device orientations and implants sites.

One of the distinguishing aspects of the invention includes the use of various shapes that are different from the long rectangular shape disclosed in U.S. Pat. No. 5,987,352. Though various shapes are proposed in this invention, each one enables easy insertion into a subcutaneous pocket or incision for implant. In addition, these shapes are implemented to enhance the sensitivity and ability to detect cardiac depolarization signals, thereby enhancing the use of a multi vector electrode configuration.

This invention also includes algorithms with significant advances over the prior art. Specifically, the invention provides user-programmable software that offers the user the ability to select the best vector to detect the greatest amplitude signal for a PQRST complex, thereby enhancing the sensing of cardiac depolarizations. At the same time, however, the user may also use the software to program a non-orthogonal vector setting, if that proves satisfactory for sensing cardiac depolarizations.

The software-configurable electrode arrangement of this invention makes it highly desirable for use when an ILR is a co-implanted device. In this type of multi-implanted device environment, information may be exchanged between the ILR and a web-based expert data center to transfer the information to a remote physician. In such a system, it becomes possible for the ILR to become a central database that triggers an appropriate therapy, provide diagnostic data, or become the source for managing chronic/current clinical case on a real-time basis.

Some of the significant aspects of the present invention include: (1) the ability to record multi-vector ECG tracings, (2) the choice of using the one vector that provides optimal signal quality, and (3) the provision of orthogonal electrode configurations that are well known for their optimal and flexible sensing. The proposed novel shapes enable without limitation (1) greater stability within the pocket and, thus, better sensing, (2) lessened sensitivity to device orientation, implant location, and motion artifacts, (3) simplicity of insertion into the pocket site, (4) a small pocket resulting in small scars, (5) a lesser likelihood of flipping within the pocket, and (6) a lesser need to suture the device within the pocket to ensure its stability.

DETAILED DESCRIPTION OF THE DRAWINGS

Figure 1:
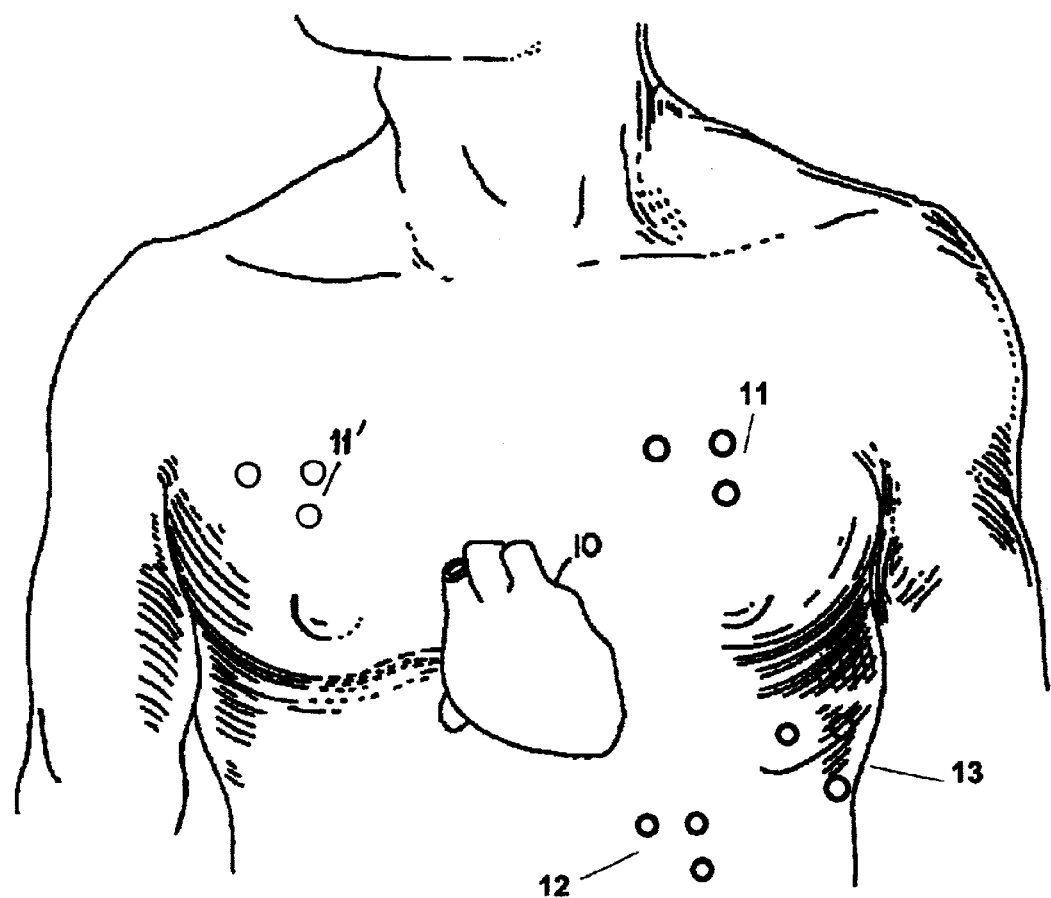
FIG. 1 is a frontal view of a patient in whom an IRL may be implanted with typical locations referenced thereon.

FIG. 1 represents the frontal view of a patient with typical implant sites. FIG. 1 also depicts how a standard ECG monitoring system may be used as a screening device in the selection of an implant site. Thus, a standard ECG Monitoring System can be used with standard electrodes and electrode preparation of the skin. The electrodes are then placed in distributed, preferably orthogonal patterns as shown at exemplary implant sites 11, 11', 12 and 13. These sites are substantially those in which an ILR may be implanted.

Orthogonal measurements over each candidate implant site may be used to determine the optimal orientation. Although a distribution of three electrodes is shown at exemplary implant locations 11, 11', 12 and 13, less than three electrodes may be used to effect the functionality of the present invention.

To determine optimal signal amplitudes, one could both simply look at the ECG signal amplitudes using the orthogonal electrodes and then assume a similar implant orientation will be substantially as "good." In the alternate, repeated attempts may be made until a satisfactory signal at a given location and orientation is obtained. Further, an alternate option would be to program using the improved vector algorithm of the present invention as will be discussed hereinbelow in order to produce the absolutely best and largest R-wave.

Figure 2:
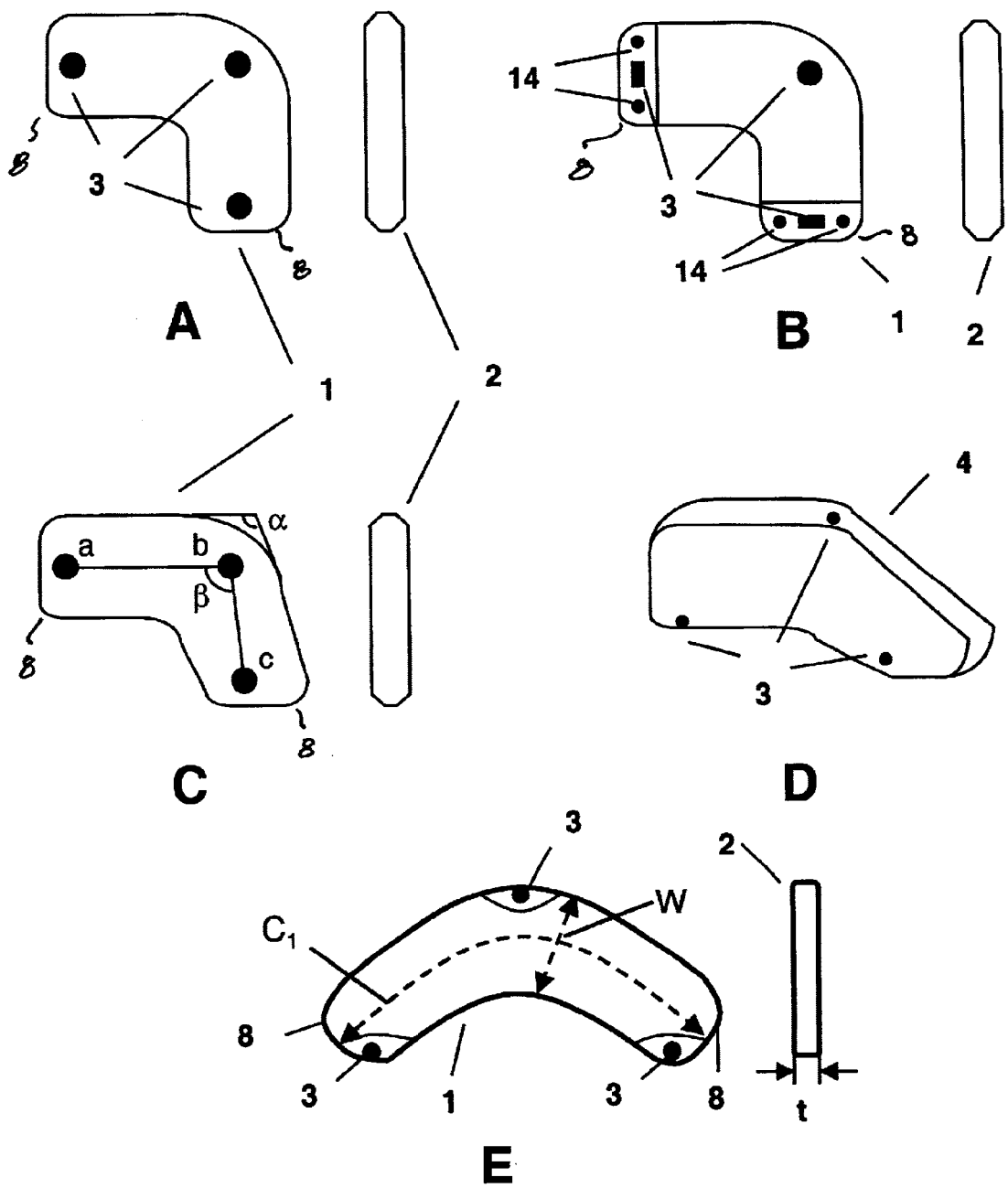
FIG. 2 shows perspective views of four embodiments of the novel configuration and the orthogonal arrangement of the electrodes of the present invention.

FIG. 2 shows perspective views of various embodiments of the configuration and the distributed, preferably orthogonal arrangement of the electrodes of the present invention. FIG. 2 (A, B, C, D, and E) represent some of the embodiments including the novel configurations/shapes of the ILR in the present invention. All configurations, however, have multiple electrodes (three in these embodiments) that are the basis of multiple sensing vectors. The electrode spacing(s), especially that between electrodes a and b (as shown in FIG. 2C) may be adjusted to approximate the spacing in the device disclosed in the '352 patent. Optimal sensing could be achieved using the spacing relations between the electrodes as enabled by the present invention. Specifically, clinical data obtained from the implementation of patent '352 may be used to configure the sense amplifiers of the present invention.

FIGS. 2A–E display front 1, side 2 of the ILR and positions of multiple electrodes 3. Multiple electrodes 3, however, may be rectangular, circular, trapezoidal or equivalent geometry in shape as shown in "wings" of the device in FIG. 2B. The configuration at the ends of each wing 8 is similar to that used in the current product disclosed in the '352 patent. In addition, suture holes 14 as shown in FIG. 2B may be provided. Suture holes 14 are used by the implanting physician to provide further stability for the device, although the novel shape of the invention is designed to provide appropriate stability within the pocket without the use of suturing.

FIG. 2C represents the angles that are preferred for optimal ILR configuration and vectors of the electrodes. Angle α establishes the angle that "wings 8" assume in the device configuration and may range from 45 to 170 degrees. Angle β establishes the angle between a–c and b–c vectors and may range from 45 to 170 degrees. The angles α and β may vary in their separate angularities within the same ILR.

FIG. 2D is a 3-D view and displays an alternative method of mounting the sensing electrodes. In this case, the electrodes are mounted on the periphery of the device. Note that, in all the embodiments, the number of sensing electrodes is not limited or restricted to three as shown in this figure. Any number of electrodes greater than two may be used to effect the implementation of the present invention.

FIG. 2E represents the preferred geometric shape of the ILR in the present invention. Specifically, the geometry promotes multi-vector sensing capabilities with a width "W" smaller than the length along a center-line axis "$C_1$". Further, the width "W" is preferably larger than the cross-sectional thickness "t". More specifically, a bend at substantially the middle of the longitudinal extent of the ILR provides a feature which in combination with the dimensional factors, enables deployment and navigation of the ILR through small incisions. Although the geometry depicted in FIG. 2E is preferred, the width "W" may vary along the central axis $C_1$. Further curvilinear wings 8 at the extremities may be shaped like arrow tips (not shown) or may be adapted to other shapes. Electrodes 3 are strategically distributed to optimally configure multi-vector sensing. The use of multiple sensing electrodes does not restrict the implementation of the present invention to an orthogonal configuration. A number of other electrodes may be placed within the perimeter of the ILR perimeter.

Figure 3:
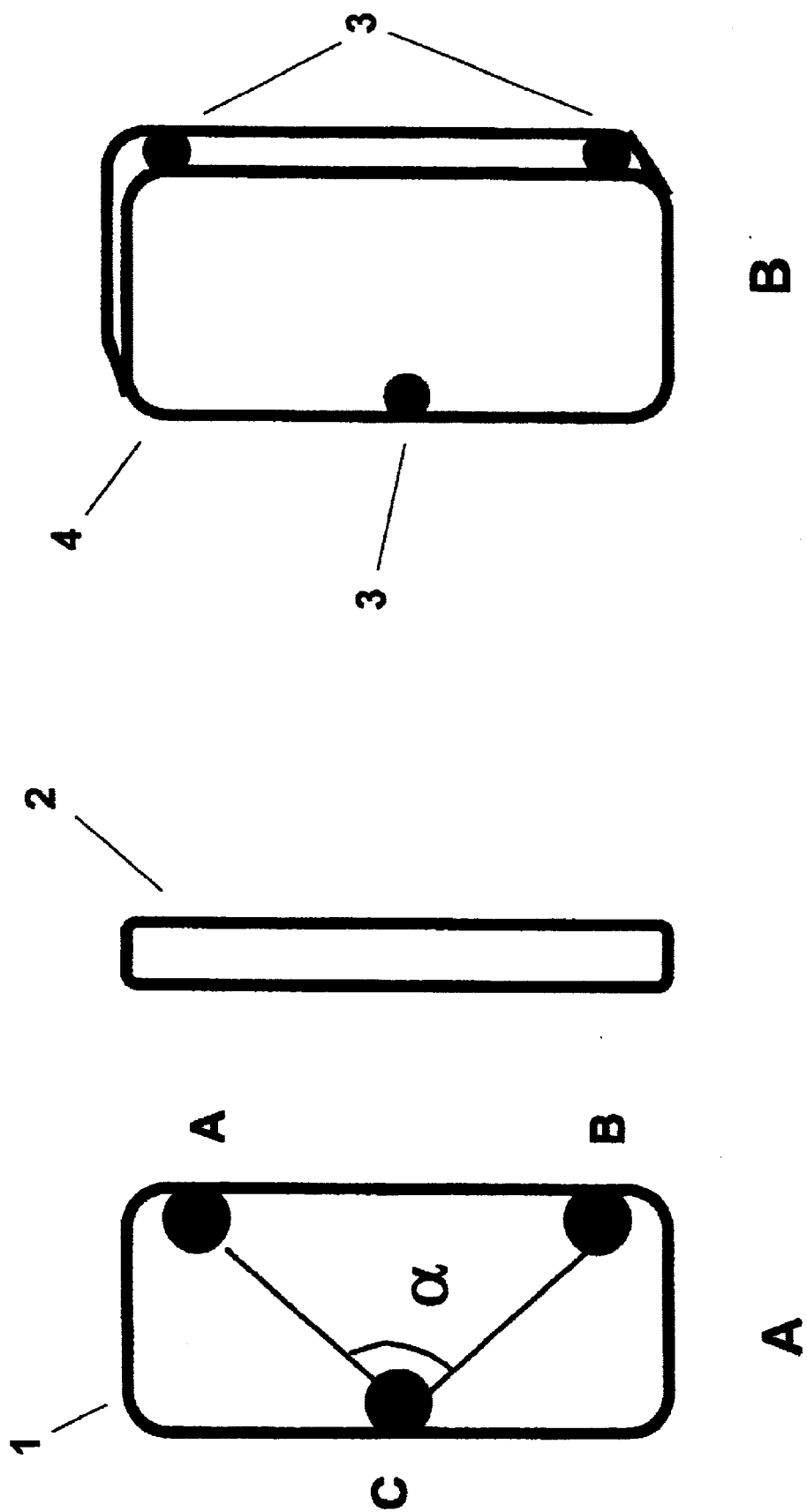
FIG. 3 is a perspective view of an alternative, rectangular configuration with the orthogonal arrangement of the electrodes of the present invention.

FIG. 3 is a perspective view of an alternative embodiment showing a rectangular configuration with an orthogonal arrangement of the electrodes. FIG. 3A represents front view 1 and side view 2. In FIG. 3A, sensing electrodes 3 are mounted on the external periphery of the casing. These electrodes form multiple sensing vectors, interacting along vectors a–b, b–c and c–a. The angle α may range from 45 to 170 degrees. The electrodes may be attached to the top or bottom of the casing with access to the internal circuits using integrated feedthroughs or other commonly known connections. In FIG. 3B sensing electrodes 3 are mounted on the periphery of the casing. In this case, the number of sensing electrodes may be more than three, although three electrodes are preferred for simplicity of manufacturing and signal processing. This embodiment enables multi-orthogonal vectors on a system with which the physician community is acquainted with and uses routinely. The system also makes it possible to eliminate the use of parylene coating on the ILR casing, as well as polyurethane header(s) to mount sensing electrodes 3 and suture holes 14 (refer to FIG. 2B). Further, this embodiment provides both design and manufacturing benefits.

Figure 4:
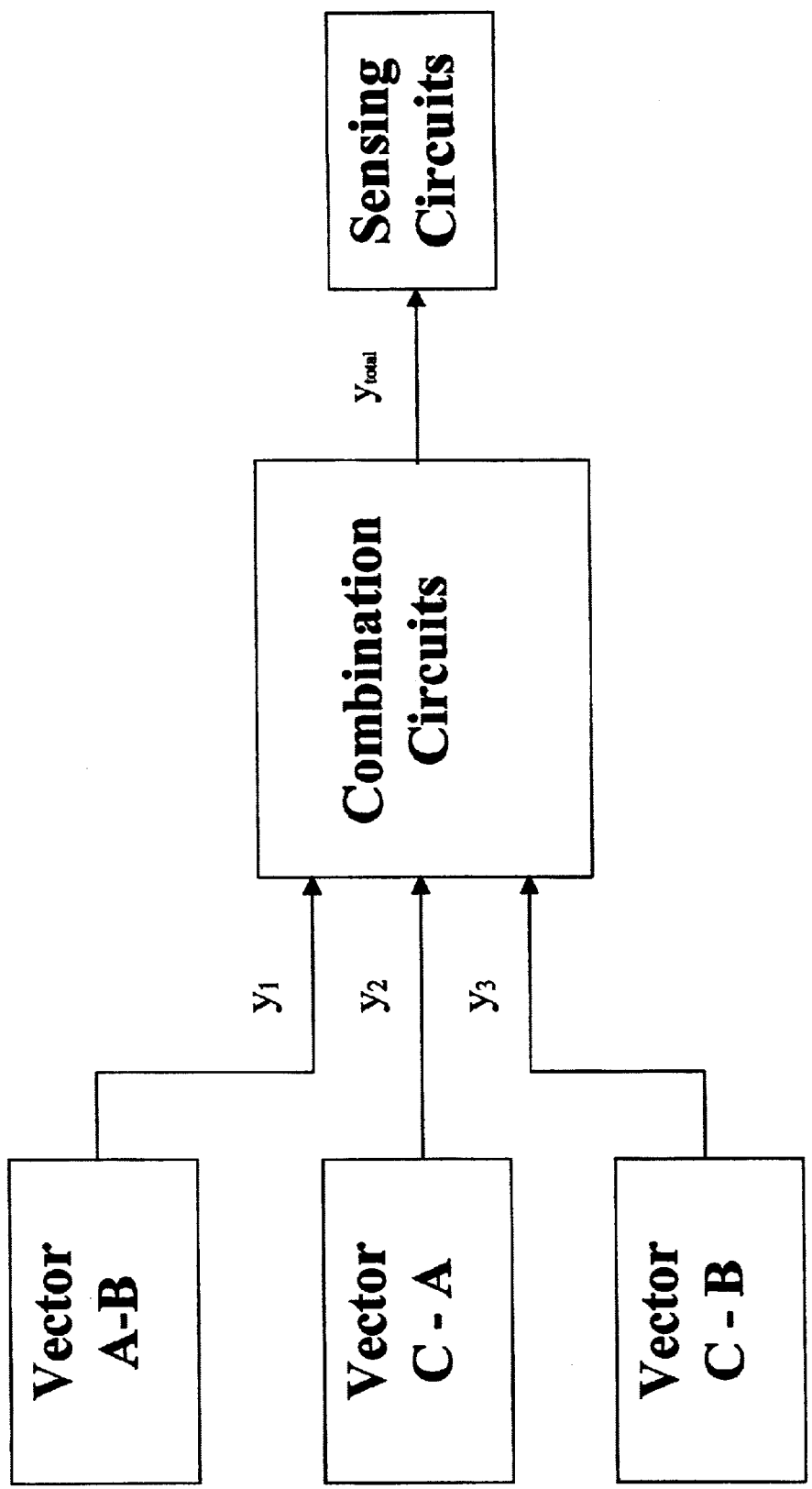
FIG. 4 is a block diagram that describes a method for combining the various ECG vectors available from the multi-vector orthogonal configuration of the sensing electrodes used in the present invention.

FIG. 4 is a block diagram representing a method for combining the various ECG vectors obtained via the multi-vector configuration of the sensing electrodes 3 of the present invention.

The following equation describes the combined signal at any given moment in instantaneous time:

$$y_{total} = \text{Max}\{|y_1|, |y_2|, \ldots, |y_i|\}$$

i=1, 2, . . . N or combination of any vectors
N=Number of vectors
$y_i$ is the ECG signal (a pair of electrodes)
$y_{total}$ is the combined signal at any instantaneous time. This signal can then be fed to another circuit for sensing R-waves (refer to in FIG. 5). Accordingly, the maximum rectified signals will be captured for appropriate sensing. In cases where the signal amplitude from one electrode pair drops dramatically, the combined circuit will preferentially and automatically switch to the other electrode pair. Users may select any combination of electrodes to establish a sensing vector from the at least more than two electrodes that are available. For example, with a total of three electrode pairs, users may determine that two of the electrode pairs will have better signal quality, such as Vector a–b ($y_1$) and Vector c–a ($y_2$). In this case, the combined signal will be:

$$y_{total} = \text{Max}\{|y_1|, |y_2|\}$$

The method and structure of the present invention used in this invention provides, inter alia, (1) user capabilities to select the signal with the best quality, including one that has the largest R-wave amplitude and R-T ratio, thus enabling qualities that promote better and more accurate diagnoses, (2) reduced computational cost that may, in turn, result in lesser power requirements, (3) adaptability to implement action in digital circuits, (4) adaptability to other sensing algorithms, such as an automatic threshold control algorithm, and (5) unlimited orientation and distribution of sensing electrodes.

Figure 5:
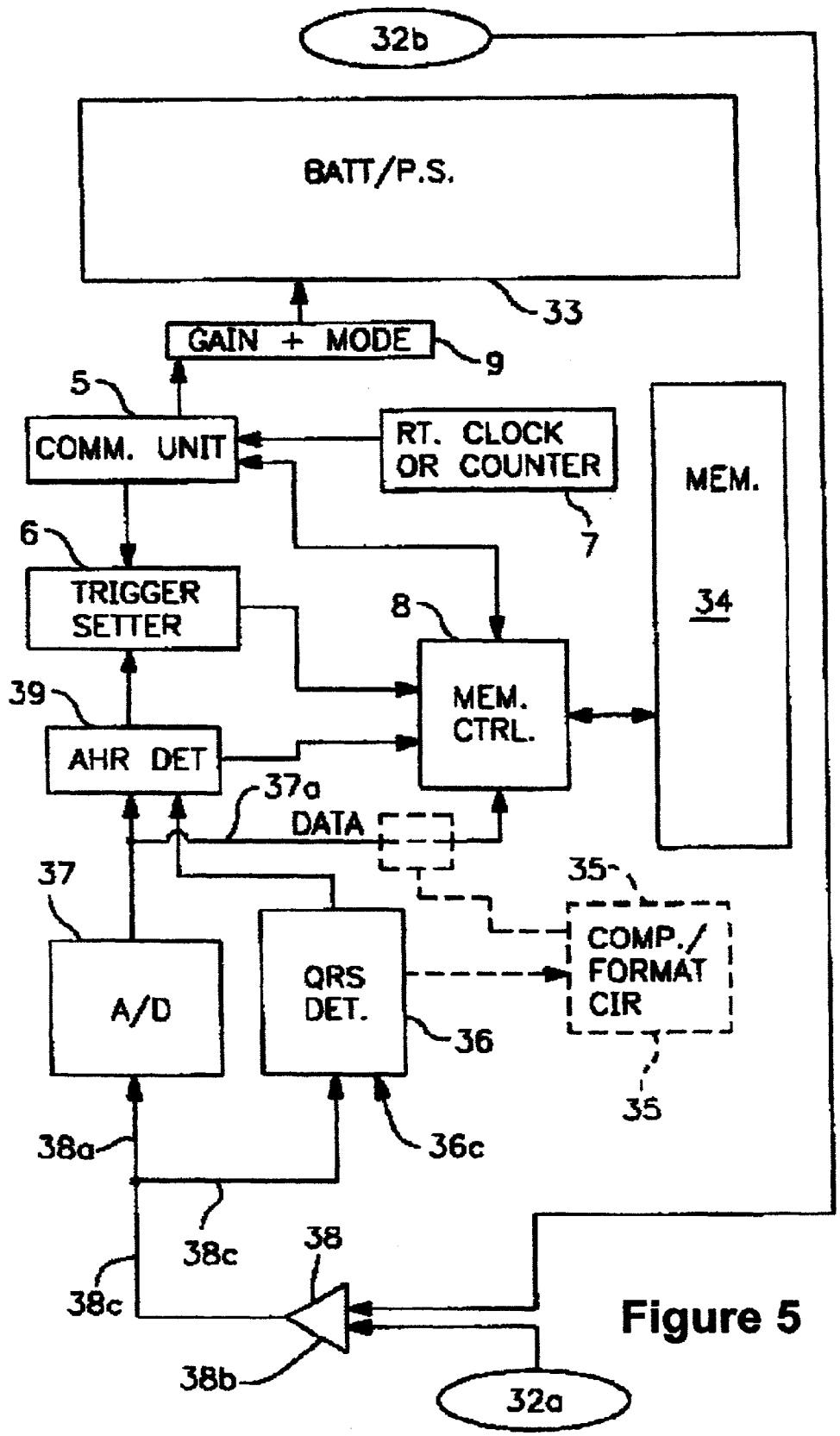
FIG. 5 is a block diagram illustrating the main circuit of a device in accord with the present invention.

FIG. 5 is a block diagram illustrating the main circuit of a device in accord with the present invention. Electrode pairs 32a and 32b ($y_1$, and $y_2$ from FIG. 4) bring signals from the body to an input mechanism 38, represented as a differential amplifier for purposes of simplicity. The output is fed to circuits including a QRS detector circuit 36 and an A/D converter circuit 37. Both these circuits 36 and 37 supply output to an arrhythmia detector 39, which in this embodiment supplies the autotrigger signal to the trigger setting circuit 6. The output data from the analog to digital converter may be converted, compressed, formatted and marked or reformulated, if desired, in circuit 35 before the data is ready for input into memory 34. Memory control circuit 8 receives input from the A/D converter, with or without conversion, from circuit 35, from the auto triggering determination circuit (here seen as the arrhythmia detection circuit) 39 (which may include input directly from the QRS detector if desired) as well as signals from the trigger setter circuit 6. The trigger setter circuit may also be controlled by a communications unit 5 which operates to receive and decode signals from the outside of the device that are telemetered or otherwise communicated into communications unit by a user. Communications unit 5 also communicates with the memory controller 8 to request the offloading of memory data 34 for analysis by an outside device, such as a programmer, expert system, etc. Communication unit 5 may therefore include any one of the many transceiver devices to transfer data from the IRL to a programmer or equivalent device. A clock or counter circuit 7 reports the time since start or real time to the outside interrogator device contemporaneously with a data offloading session so that the events recorded in memory 34 may be temporally pinpointed.

While the invention has been described above in connection with the preferred embodiments and examples thereof, one skilled in the art will appreciate that the invention is not limited to the embodiments disclosed herein. It will thus be understood that numerous other embodiments, examples, uses, modifications of, and variations from, the disclosure may be made without departing the scope of the present invention as claimed herein. As to every element, it may be replaced by any one infinite equivalent alternatives only some of which are disclosed in the specification.

What is claimed is:

1. An implantable medical device (IMD) including a plurality of sensing electrodes configured for multi-vector sensing forming an insertable loop recorder (ILR) in combination, the IMD comprising:

a geometric body having a thickness smaller than its width and wherein said width is smaller than a length defined along a center-line axis, the body including a bend, a first wing extending from a first side of the bend and a second wing extending from a second side of the bend; and a plurality of electrodes coupled to said geometric body such that a first electrode of the plurality is positioned on the first wing, a second electrode of the plurality is positioned on the second wing and a third electrode of the plurality is positioned proximate to the bend;

wherein a line extending from the first electrode to the third electrode forms an angle with a line extending from the second electrode to the third electrode, the angle being between and including 45 degrees and 100 degrees; and whereby said electrodes form multi-vector relations and said geometric body is adapted for ease of subcutaneous insertion in a patient's body and for positional stability within the patient's body to thereby sense physiological signals via said electrodes.

2. The IMD of claim 1 wherein the wings form substantially curvilinear edges.

3. The IMD of claim 1 wherein said multi-vector relations include a rule-based software program implemented to select from said multi-vector relations at least one vector relation.

4. The IMD of claim 1, wherein the bend is located in proximity to a mid-point of the center-line axis of the body.

5. The IMD of claim 1, wherein the first electrode and the second electrode are positioned on a first side of the center-line axis and the third electrode is positioned on a second side of the center-line axis.

6. The IMD of claim 1, wherein the body further includes a side spanning the width of the body and at least one of the plurality of electrodes is positioned on the side.

7. The IMD of claim 1, wherein the body further includes a side spanning the thickness of the body and at least one of the plurality of electrodes is positioned on the side.

8. The IMD of claim 1, wherein one or both of the first wing and the second wing includes at least one suture hole.

9. The IMD of claim 1, wherein the plurality of electrodes includes only three electrodes.

* * * * *